United States Patent [19]

Kurozumi et al.

[11] Patent Number: 4,734,436
[45] Date of Patent: Mar. 29, 1988

[54] BENZOYLPHENYLUREA DERIVATIVE AND ITS USE AS AN INSECTICIDE

[75] Inventors: Akira Kurozumi, Tokyo; Satoshi Ototake, Ohmiya; Hitoshi Sato, Ageo; Satoshi Tanabe, Ageo; Tatsumi Hayaoka, Ageo; Akio Masui, Ohmiya, all of Japan

[73] Assignee: Nippon Kayaku Kabushiki Kaisha, Tokyo, Japan

[21] Appl. No.: 806,601

[22] Filed: Dec. 9, 1985

[30] Foreign Application Priority Data

Dec. 21, 1984 [JP] Japan ................ 59-268435

[51] Int. Cl.$^4$ .......... C07C 157/12; C07C 127/22; A01N 47/34
[52] U.S. Cl. .................. 514/594; 564/44; 564/23; 514/584
[58] Field of Search ............ 564/44, 23; 514/594

[56] References Cited

U.S. PATENT DOCUMENTS

| 3,686,418 | 8/1972 | Taber et al. ............... 424/322 |
| 3,748,356 | 7/1973 | Wellinga et al. ........... 260/553 E |
| 3,793,213 | 2/1974 | Taber et al. ............... 252/107 |
| 3,989,842 | 11/1976 | Wellinga et al. ............ 424/322 |
| 4,013,717 | 3/1977 | Wellinga et al. ............ 564/44 |
| 4,085,226 | 4/1978 | Sirrenberg et al. .......... 564/44 |
| 4,276,310 | 6/1981 | Sirrenberg et al. .......... 564/44 |
| 4,399,152 | 8/1983 | Brouwse et al. ............. 564/44 |
| 4,457,943 | 7/1984 | Becher et al. .............. 514/594 |
| 4,529,819 | 7/1985 | Clifford et al. ............ 564/44 |
| 4,533,676 | 8/1985 | Sirrenberg et al. .......... 564/44 |

FOREIGN PATENT DOCUMENTS

| 0008435 | 8/1979 | European Pat. Off. ............. 564/23 |
| 88343 | 9/1983 | European Pat. Off. ............. 514/594 |
| 123302 | 10/1984 | European Pat. Off. ............. 564/44 |
| 126418 | 8/1982 | Japan . | |

OTHER PUBLICATIONS

Journal of Agriculture and Food Chemistry, vol. 24, No. 5, pp. 1065-1068 (1976).

Primary Examiner—Floyd D. Higel
Assistant Examiner—Carolyn S. Greason
Attorney, Agent, or Firm—Henry C. Nields

[57] ABSTRACT

Disclosed is a compound of the formula:

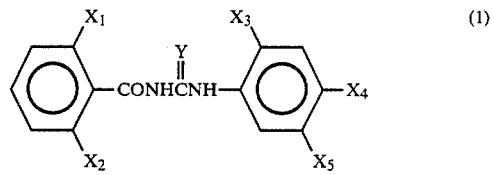

wherein $X_1$ and $X_3$ represent chloro or fluoro, $X_2$ represents hydrogen, chloro or fluoro, $X_4$ represents hydrogen or halogen, $X_5$ represents $-CF_3$ or $-OCF_3$, Y represents oxygen or sulfur and an insecticidal composition containing said compound, a method for killing insect pests and a process for producing said compound and its use as pesticide.

2 Claims, No Drawings

BENZOYLPHENYLUREA DERIVATIVE AND ITS USE AS AN INSECTICIDE

DETAILED DESCRIPTION OF THE INVENTION

This invention relates to a compound of the formula:

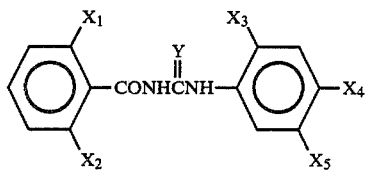

wherein $X_1$ and $X_3$ represent chloro or fluoro, $X_2$ represents hydrogen, chloro or fluoro, $X_4$ represents hydrogen or halogen, $X_5$ represents —$CF_3$ or —$OCF_3$, Y represents oxygen or sulfur and an insecticidal composition containing said compound, a method for killing insect pests and a process for producing said compound.

The present invention relates to new benzoylphenylurea derivatives usable as pesticides in paddy fields, uplands, orchards, forests and cattle sheds.

It has been known that benzoylphenylurea derivatives are effective on insect pests resistant to organophosphorus, carbamate and pyrethroid insecticides. For example, it is described in J. Agr. Food Chem., 21 (6), 993 (1973) that N-(p-chlorophenyl)-N'-(2,6-difluorobenzoyl)urea (generally called "diflubenzuron") has an insecticidal activity on yellow fever mosquito (*Aedes aegypti L.*), large white (*Pieris brassicae L.*) and Colorado potato beetle (*Leptinotarsa decemlineata Soy*).

However, the benzoylphenylurea derivatives sold on the market have a defect that their insecticidal spectrum is limited to a narrow range, when they are used in a low concentration.

The present invention provides pesticides free of said defect.

The inventors have found that benzoylphenylurea derivatives of the general formula:

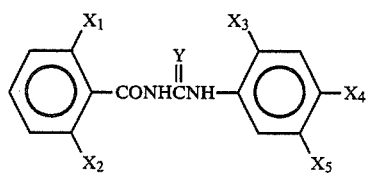

wherein $X_1$ and $X_3$ represents each a chlorine or fluorine atom, $X_2$ represents a hydrogen, chlorine or fluorine atom, $X_4$ represents a hydrogen or halogen atom, $X_5$ represents —$CF_3$ or —$OCF_3$ and Y represents an oxygen or sulfur atom, are pesticides having a wide pesticidal spectrum and a high activity even in a low concentration.

The compounds of the above general formula (1) can be produced by the following processes (a) and (b):

Process (a): This process comprises reacting a 2,4,5-substituted aniline of the formula:

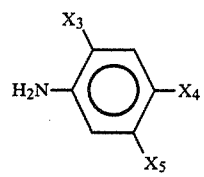

wherein $X_3$, $X_4$ and $X_5$ have the same meaning as above, with a 2,6-substituted benzoyl isocyanate or 2,6-substituted benzoyl isothiocyanate of the formula:

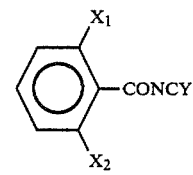

wherein $X_1$, $X_2$ and Y have the same meaning as above.

This process can be carried out easily by dissolving the substituted aniline of the above formula (2) preferably in an inert solvent and adding dropwise a solution of the 2,6-substituted benzoyl isocyanate or 2,6-substituted benzoyl isothiocyanate of the above formula (3) in an inert solvent to said solution at $-5°$ C. to $100°$ C., preferably $0°$ to $40°$ C.

Examples of the inert solvents include aromatic hydrocarbons such as benzene, toluene, xylene, monochlorobenzene and dichlorobenzene; esters such as ethyl acetate; nitriles such as acetonitrile; n-hexane; ketones such as acetone; aliphatic chlorinated hydrocarbons such as carbon tetrachloride and perclene; and ethers such as dioxane and tetrahydrofuran.

After completion of the reaction, the product is treated in an ordinary manner to obtain the intended product.

The substituted benzoyl isocyanates and isothiocyanates of the formula (3) used as the starting material are known compounds which can be produced by a conventional process [J. Org. Chem., 30 (12), 4306-7 (1965) and J. Am. Chem. Soc., 61, 632 (1939)].

The 2,4,5-substituted anilines of the formula (2) can be produced according to the following reactions:

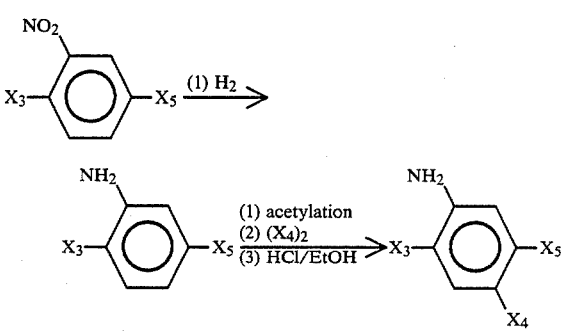

wherein $X_3$ represents a fluorine or chlorine atom, $X_4$ represents a fluorine, chlorine or bromine atom and $X_5$ represents —$CF_3$ or —$OCF_3$.

Process (b): This process comprises reacting a 2,4,5-substituted phenyl isocyanate or isothiocyanate of the formula:

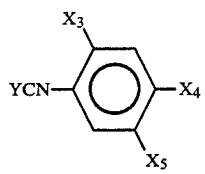  (4)

wherein $X_3$, $X_4$, $X_5$ and Y have the same meaning as above, with a 2,6-substituted benzamide of the formula:

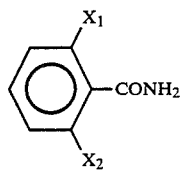  (5)

wherein $X_1$ and $X_2$ have the same meaning as above.

In this process, the both starting compounds are dissolved preferably in the above-mentioned inert solvent and reacted at 30° to 180° C., preferably 40° to 150° C., for 1 to 24 h.

The 2,4,5-substituted phenyl isocyanates and isothiocyanates used as the starting materials of the above formula (4) can be produced from corresponding anilines by an ordinary proces [Yuki Gosei Kagaku Kyokai-shi, 34, 431 (1976) and J. Am. Chem. Soc. 54, 781 (1932)]. Among the compounds of the formula (1) of the present invention, preferred are the following compounds:

(A) when Y in the formula (1) is oxygen:
  $X_1$ and $X_2$ are chloro or fluoro,
  $X_2$ is hydrogen, chloro or fluoro,
  $X_4$ is hydrogen or halogen,
  $X_5$ is $-CF_3$ or $-OCF_3$
(B) when Y in the formula (1) is sulfur:
  $X_1$ is chloro or fluoro,
  $X_2$ is hydrogen, chloro or fluoro,
  $X_3$ is fluoro,
  $X_4$ is fluoro, chloro or bromo,
  $X_5$ is $-CF_3$ or $-OCF_3$ and Among the compounds of the formula (1), more preferred are the following compounds:

(C) when Y in the formula (1) is oxygen:
  $X_1$, $X_2$ and $X_3$ are fluoro,
  $X_4$ is fluoro, chloro or bromo,
  $X_5$ is $-CF_3$ or $-OCF_3$
(D) when Y in the formula (1) is sulfur:
  $X_1$, $X_2$ and $X_3$ are fluoro,
  $X_4$ is a chloro, fluoro or bromo,
  $X_5$ is $-CF_3$ or $-OCF_3$ and The most preferred compounds of the formula (1) are those of the following formulae:

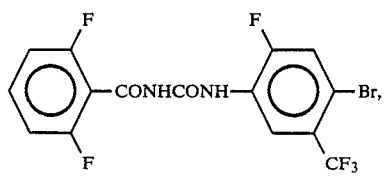

-continued

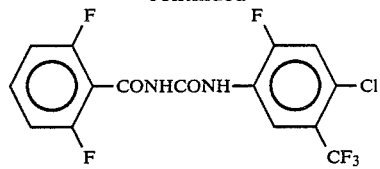

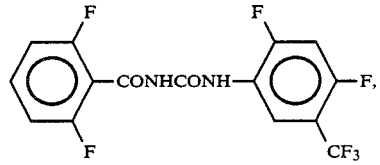

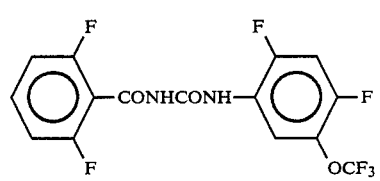

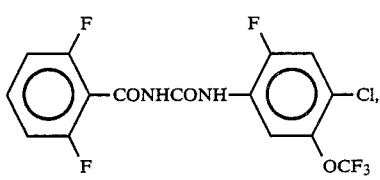

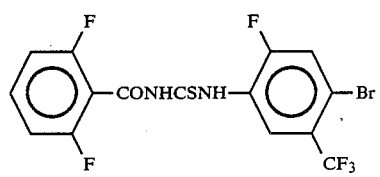

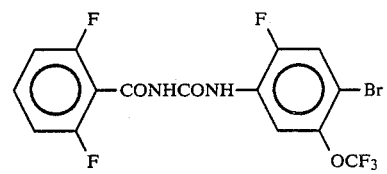

The compounds of the general formula (1) of the present invention may be used as the pesticides as they are or in the form of a mixture with an adjuvant to improve or stabilize their effects depending on the use of them. They may be formulated into, for example, a dust, fine granule, granule, wettable powder, flowable liquids, emulsifiable concentration or toxic feed.

In the practical application of these various products, they may be used as such or after dilution with water into a desired concentration.

The pesticidal adjuvants used herein include a carrier (diluent) and other adjuvants such as spreader, emulsifier, wetting agent, dispersant, fixing agent and disintegrator. Examples of the liquid carriers include aromatic hydrocarbons such as toluene and xylene; alcohols such as butanol, octanol and glycol; ketones such as acetone; amides such as dimethylformamide; sulfoxides such as dimethyl sulfoxide; methylnaphthalene; cyclohexanone; animal and vegetable oils; fatty acids; fatty acid esters; petroleum fractions such as kerosene and gas oil; and water. Examples of the solid carriers include clay, kaolin, talc, diatomaceous earth, silica, calcium carbonate, montmorillonite, bentonite, feldspar, quartz, alumina and sawdust.

As the emulsifiers and dispersants, surfactants are used usually. They include anionic, cationic, nonionic and amphoteric surfactants such as sodium higher alcohol sulfates, stearyltrimethylammonium chloride, polyoxyethylene alkylphenyl ethers and laurylbetaine.

Examples of the spreaders include polyoxyethylene nonylphenyl ethers and polyoxyethylene lauryl ethers. Examples of the wetting agent include polyoxyethylene nonylphenyl ether dialkylsulfosuccinates. The fixing agents are carboxymethylcellulose, polyvinyl alcohols, etc. and the disintegrators are sodium ligninsulfonate, sodium laurylsulfonate, etc.

The pesticides of the present invention may be used as such or in the form of a mixture with a fungicide, insecticide, acaricide, herbicide, plant growth regulator, soil disinfectant, soil conditioner or nematocide as well as a fertilizer or another pesticide.

The pesticidal activity can be increased several times when synergists for pyrethroids such as piperonyl butoxide, sulfoxide or safroxane are added.

The concentration of the active ingredient in the composition of the present invention varies depending on the form of the pesticide, manner of the application and other conditions. Though the active ingredient may be used alone, it is used in an amount of usually 0.2 to 95 wt. %, preferably 0.5 to 30 wt. %, based on the composition.

The amount of the composition of the present invention to be used varies depending on the form of the pesticide, manner of the application, period and other conditions. It is used in an amount of 0.1 to 100 g, preferably 1.0 to 50 g (in terms of the active ingredient) for 10 a (a=100 m$^2$) for the control of ornamental, forest or livestock insect pests and in an amount of 0.01 to 10 mg, preferably 0.02 to 5 mg/m$^2$ (in terms of the active ingredient) for the purpose of exterminating hygienic insect pests. For example, the amounts of the dust, granules and emulsifiable concentrate or wettable powder are 0.1 to 50 g, 0.2 to 100 g and 0.1 to 100 g in terms of the active ingredient, respectively, for 10 a. In an exceptional case, they may be or even should be used in an amount outside said ranges.

Typical examples of pests to which the pesticides of the present invention are applicable are as follows:

(1) Lepidoptera: apple leafminer (*Phyllonorycter ringoneella*), diamond back moth (*Plutella xylostella*), cotton seed worm (*Promalactis inonisema*), smaller tea tortirx(Adoxophyes sp.), soybean pod borer (*Leguminivora glycinivorella*), rice leafroller (*Cnaphalocrocis medinalis*), rice stem borer (*Chilo suppressalis*), oriental corn borer (*Ostrinia furnacalis*), cabbage armyworm (*Mamestra brassicae*), armyworm (*Pseudaletia separata*), common cutworm (*Spodoptera litura*), rice skipper (*Parnara guttata*) and common cabbageworm (*Pieris rapae crucivora*), (2) Coleoptera: cupreous chafer (*Anomala cuprea*), Japanese beetle (*Popillia japonica*), rice plant weevil (*Echinocnemus squameus.*), rice water weevil (*Lissorhoptrus oryzophilus*), rice leaf beetle (*Oulema oryzae*), varied carpet beetle (*Anthrenus verbasci*), cadelle (*Tenebroides mauritanicus*), maize weevil (*Sitophilus zeamais*), twenty-eight-spotted ladybird (*Henosepilachna vigintioctopunctata*), adzuki bean weevil (*Callosobruchus chinensis*), Japanese pine sawyer (*Monochamus alternatus*) and cucurbit leaf beetle (*Aulacophora femoralis*), (3) Diptera: tropical mosquito (*Culex pipiens fatigans*), yellow fever mosquito (*Aedes aegypti*), house mosquito (*Culex plipiens molestus*), soybeam pod gall midge (*Asphondylia sp.*) seedcorn maggot (*Hylemya platura*) housefly (*Musca domestica*), melon fly (*Dacus cucurbitae*) and rice leafminer (*Agromyza oryzae*), (4) Orthoptera: mole cricket (*Gryllotalpa africana*), migratory locust (*Locusta migratoria*), short-winged rice grasshopper (*Oxya yezoensis*), German cockroach (*Blattella germanica*) and smoky brown cockroach (*Periplaneta fuliginoza*), (5) Hymenoptera: cabbage sawfly (*Athalia rosae japonensis*) and azalea sawfly (*Arge similis*), (6) Tylenchida: soybean cyst nematode (*Heterodera glycines*), rice cyst nematode (*Heterodera oryzae*), cotton root-knot nematode (*Meloidogyne incognita*), root-lesion nematode (*Pratylenchus neglectus*), rice white tip nematode (*Aphelenchoides besseyi*), chrysanthemum leaf nematode (*Aphelenchoides besseyi*), chrysanthemum leaf nematode (*Aphelenchoides ritzemabosi*) and pine wood nematode (*Bursaphelenchus lignicolus*), and (7) Hemiptera: green rice leafhopper (*Nephotettix cincticeps*), white backed rice planthopper (*Sogatella furcifera*), small brown planthopper (*Laoderphax striatellus*), brown rice planthopper (*Nilapar vata lugens*), bean bug (*Riptortus clavatus*), southern green stink bug (*Nezara viridula*), pear lace bug (*Stephanitis nashi*), greenhouse whitefly (*Trialeurodes vaporariorum*), cotton aphid (*Aphis gossypii*), green peach aphid (*Myzus persicae*) and arrowhead scale (*Unaspis yanonensis*).

The compound of the present invention can be applied to insect pests or locus thereof. As will be shown by the following tests, the compounds of the formula (1) of the present invention have pesticidal effects superior to those of the benzoylphenylurea derivatives used heretofore.

The following examples will further illustrate the present invention.

SYNTHESIS EXAMPLE 1

Production of 4-bromo-2-chloro-5-trifluoromethylaniline:

3.9 g (0.02 mol) of 2-chloro-5-trifluoromethylaniline and 3.1 g (0.03 mol) of acetic anhydride were stirred in 40 ml of acetic acid at room temperature for 2 h and then the temperature was raised to 110° C. 3.5 g (0.022 mol) of bromine was added dropwise thereto at 110° C. After completion of the reaction the reaction mixture was poured into water, extracted with benzene and washed with water. After removal of the solvent, 30 ml of ethanol and 30 ml of conc. hydrochloric acid were added to the residue and the mixture was heated under refluxing for 1 h. After cooling, the reaction mixture was neutralized with a 10% aqueous sodium hydroxide solution, extracted with benzene and washed with water and brine. The solvent was removed under reduced pressure and the residue was purified by distillation.

Yield: 5.4 g.

B.P.: 119°~121° C./28 mmHg.

SYNTHESIS EXAMPLE 2

Production of N-(4-bromo-2-fluoro-5-trifluoromethylphenyl)-N'-(2,6-difluorobenzoyl)urea:

2.58 g (0.01 mol) of 4-bromo-2-fluoro-5-trifluoromethylaniline obtained in the same manner as in Synthesis Example 1 was dissolved in 40 ml of toluene. 3.9 g (0.0105 mol) of a 50% solution of 2,6-difluorobenzoyl isocyanate in toluene was added dropwise to the solution with stirring below 10° C. After stirring at 25° C. for 1 h, the precipitate was formed and filtered. After the recrystallization from ethyl acetate, 3.9 g (90% yield) of colorless crystals were obtained. Melting point: 208° to 210° C.

SYNTHESIS EXAMPLE 3

Production of N-(4-bromo-2-chloro-5-trifluoromethylphenyl)-N'-(2,6-difluorobenzoyl)urea:

4.8 g (0.016 mol) of 4-bromo-2-chloro-5-trifluoromethylphenyl isocyanate and 50 ml of toluene were added to 2.36 g (0.015 mol) of 2,6-difluorobenzamide and the mixture was heated under refluxing for 20 h.

After cooling the precipitate was formed and filtered. After the recrystallization from ethyl acetate, 5.8 g (85% yield) of colorless, crystals were obtained. m.p.: 184° to 187° C.

SYNTHESIS EXAMPLE 4

Production of N-(4-bromo-2-fluoro-5-trifluoromethylphenyl)-N'-(2,6-difluorobenzoyl)thiourea:

1.2 g of potassium thiocyanate was dissolved in 20 ml of dry acetone. A solution of 1.8 g (0.01 mol) of 2,6-difluorobenzoyl chloride in 5 ml of acetone was added dropwise to the solution with stirring at room temperature. After completion of the addition, the mixture was heated under refluxing for 10 min and then a solution of 2.6 g (0.01 mol) of 4-bromo-2-fluoro-5-trifluoromethylaniline in 10 ml of acetone was added dropwise thereto at such a rate that the reaction mixture was refluxed slowly. The refluxing was continued for additional 20 min, cooled and the reaction mixture was poured into an ice/water. Crystals thus formed were filtered, washed with water and ethanol and dried. After the recrystallization from toluene, 3.7 g (81% yield) of colorless crystals were obtained. m.p.: 161° to 163° C.

Compounds shown in Table 1 were produced in the same manner a above.

TABLE 1

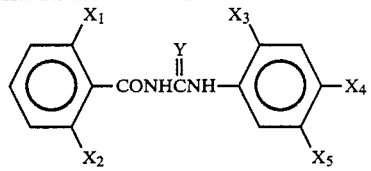

| No. | $X_1$ | $X_2$ | $X_3$ | $X_4$ | $X_5$ | Y | Physical properties | |
|---|---|---|---|---|---|---|---|---|
| 1 | F | F | F | H | $CF_3$ | O | colorless crystal | 190–1° C. |
| 2 | F | F | F | Br | $CF_3$ | O | colorless crystal | 208–10° C. |
| 3 | F | F | Cl | Br | $CF_3$ | O | colorless crystal | 184–7° C. |
| 4 | F | F | Cl | Cl | $CF_3$ | O | colorless crystal | 176–8° C. |
| 5 | Cl | Cl | F | Br | $CF_3$ | O | colorless crystal | 233–5° C. |
| 6 | Cl | Cl | Cl | Br | $CF_3$ | O | colorless crystal | 225–7° C. |
| 7 | Cl | H | F | Br | $CF_3$ | O | colorless crystal | 196–8° C. |
| 8 | F | F | F | F | $CF_3$ | O | colorless crystal | 192–3° C. |
| 9 | F | F | F | Cl | $CF_3$ | O | colorless crystal | 210–2° C. |
| 10 | F | F | F | Br | $CF_3$ | S | colorless crystal | 161–3° C. |
| 11 | F | F | F | F | $CF_3$ | S | colorless crystal | 141–2° C. |
| 12 | F | F | F | F | $OCF_3$ | O | colorless crystal | 168–9° C. |
| 13 | F | F | F | Br | $OCF_3$ | O | pale yellow crystal | 156–9° C. |
| 14 | F | F | F | F | $OCF_3$ | S | pale yellow crystal | 122–4° C. |

FORMULATION EXAMPLE 1

5% Emulsifiable Concentrate 80 parts of dimethyl sulfoxide and 15 parts of a mixture of an alkylphenol/ethylene oxide condensate and a calcium alkylbenzenesulfonate (8:2) (trade name: L-1515-2H; a product of Takemoto Yushi Co.) were added to 5 parts of N-(4-bromo-2-fluoro-5-trifluoromethylphenyl)-N'-(2,6-difluorobenzoyl)urea to obtain an emulsifiable concentrate.

This is spread after dilution with water to 1/1000 to 1/4000 concentration.

FORMULATION EXAMPLE 2

20% Wettable powder 54 parts of kaolin, 20 parts of diatomaceous earth, 3 parts of sodium ligninsulfonate and 3 parts of sodium dodecylbenzenesulfonate were added to 20 parts of N-(4-bromo-2-fluoro-5-trifluoromethylphenyl)-N'-(2,6-difluorobenzoyl)urea to obtain a wettable powder.

This wettable powder is spread after dilution with water to 1/1000 to 1/4000 concentration.

FORMULATION EXAMPLE 3

20% Flowable liquid 20 parts of ethylene glycol, 3 parts of sodium ligninsulfonate, 3 parts of sodium dodecylbenzenesulfonate, 0.1 part of an antifoaming agent (trade name: Pelex RP; a product of Kao Sekken) and 56.9 parts of water were added to 20 parts of N-(4-bromo-2-fluoro-5-trifluoromethylphenyl)-N'-(2,6-difluorobenzoyl)ure to obtain a flowable liquid.

This product is spread after dilution with water to 1/1000 to 1/4000 concentration.

TEST EXAMPLE 1

Effect on third instar larvae of diamond back moth (*Plutella xylostella*):

Two cabbage leaves of the penta- to hexafoliate stages were dipped in an aqueous solution obtained by diluting the 5% emulsifiable concentrate of the compound of the present invention in Table 1 or a control compound to a given concentration (5.0 ppm) for 10 sec. After air-drying, the cabbage leaves were placed in a plastic container having a height of 5 cm. Then, ten larvae (third instar) of the diamond back moth were put in the container. The container was left to stand in a temperature-controlled room at 25° C. After 4 days, the number of dead insects was counted to calculate the mortality. The results are ranked as follows:

Mortality

A: 90% or higher
B: from 50% to less than 90%
C: from 20% to less than 50%
D: less than 20%

As control compounds, diflubenzuron (control A) and N-(4-bromo-2-fluorophenyl)-N'-(2,6-difluorobenzoyl)urea (control B) (a compound disclosed in the specification of Japanese Patent Laid-Open No. 148847/1983) were used.

The results are shown in Table 2.

TABLE 2

| Effect on third larvae of diamond back moth | |
|---|---|
| Compound | Effect Mortality (5.0 ppm) |
| Control Compound A | D |
| Control Compound B | D |
| Compound 2 | A |
| Compound 4 | A |
| Compound 7 | A |
| Compound 8 | A |
| Compound 9 | A |
| Compound 10 | A |
| Compound 11 | A |
| Compound 12 | A |
| Compound 13 | A |
| Compound 14 | A |

TEST EXAMPLE 2

Effect on third instar larvae of common cutworm

Five cabbage leaves were dipped in an aqueous solution of a given concentration of the compound of the present invention and a control (1.0 ppm). After air-drying, the leaves were placed in a plastic container having a size of 10×15×5 (height) cm and ten of third instar larvae of common cutworm were transferred to the container in the same manner as in Test Example 1. After 4 days, the number of dead insects was counted. The ranking of the results were the same as in Test Example 1. The results are shown in Table 3.

TABLE 3

| Effect on third instar larvae of common cutworm | |
|---|---|
| Compound | Effect Mortality (1.0 ppm) |
| Control compound A | C |
| Control compound B | B |
| Compound 1 | A |
| Compound 2 | A |
| Compound 3 | A |
| Compound 4 | A |
| Compound 7 | B |
| Compound 8 | A |
| Compound 9 | A |
| Compound 10 | A |
| Compound 11 | A |
| Compound 12 | A |

TABLE 3-continued

| Effect on third instar larvae of common cutworm | |
|---|---|
| Compound | Effect Mortality (1.0 ppm) |
| Compound 13 | A |
| Compound 14 | A |

TEST EXAMPLE 3

Effect on larvae of house mosquitoes:

200 ml of well water was placed in a plastic cup having a diameter of 9 cm. Twenty of third instar larvae of house mosquito (obtained in Ageo city) were put therein and a 20% wettable powder of a compound of the present invention shown in Table 1 or the same control compound as in Test Example 1 was added thereto to realize a given concentration (0.01 ppm). After one week, the number of dead insects was counted. The results are shown in Table 4.

The ranking of results were the same as in Test Example 1.

TABLE 4

| Effect on larvae of house mosquito | |
|---|---|
| Compound | Effect Mortality (0.01 ppm) |
| Control compound A | C |
| Control compound B | B |
| Compound 1 | A |
| Compound 2 | A |
| Compound 3 | A |
| Compound 4 | A |
| Compound 5 | A |
| Compound 7 | A |
| Compound 8 | A |
| Compound 9 | A |
| Compound 10 | A |
| Compound 11 | A |
| Compound 12 | A |
| Compound 13 | A |
| Compound 14 | A |

What we claim is:

1. A compound of the formula:

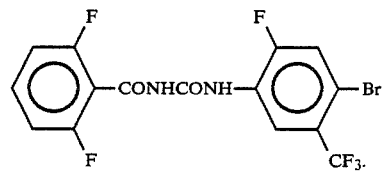

2. A pesticidal composition which comprises, as an effective component, a pesticidally effective amount of a compound of the formula:

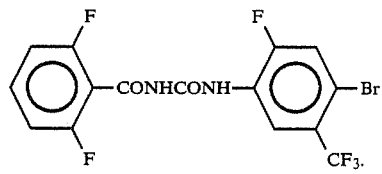

* * * * *